United States Patent
Mackenroth et al.

(10) Patent No.: US 9,079,822 B2
(45) Date of Patent: Jul. 14, 2015

(54) PROCESS FOR THE PREPARATION OF NITRATED AROMATICS AND MIXTURES THEREOF

(75) Inventors: Wolfgang Mackenroth, Tervuren (BE); Johannes Buettner, Ruhland (DE); Eckhard Stroefer, Mannheim (DE); Wolfgang Voigt, Weissenborn (DE); Frank Bok, Freiberg (DE)

(73) Assignee: BASF SE, Ludwigshafen (DE)

(*) Notice: Subject to any disclaimer, the term of this patent is extended or adjusted under 35 U.S.C. 154(b) by 214 days.

(21) Appl. No.: 13/203,360

(22) PCT Filed: Feb. 26, 2010

(86) PCT No.: PCT/EP2010/052450
§ 371 (c)(1),
(2), (4) Date: Aug. 25, 2011

(87) PCT Pub. No.: WO2010/097453
PCT Pub. Date: Sep. 2, 2010

(65) Prior Publication Data
US 2011/0306795 A1     Dec. 15, 2011

(30) Foreign Application Priority Data
Feb. 26, 2009 (EP) .................................... 09153699

(51) Int. Cl.
C07C 209/00 (2006.01)
C07C 201/08 (2006.01)

(52) U.S. Cl.
CPC .................................... C07C 201/08 (2013.01)

(58) Field of Classification Search
None
See application file for complete search history.

(56) References Cited

U.S. PATENT DOCUMENTS

| | | | |
|---|---|---|---|
| 4,091,042 A | 5/1978 | Alexanderson et al. | |
| 4,804,792 A | 2/1989 | Mason et al. | |
| 5,099,078 A | 3/1992 | Quakenbush | |
| 5,099,079 A | 3/1992 | Quakenbush | |
| 5,728,901 A | 3/1998 | Ramprasad et al. | |
| 5,763,687 A | 6/1998 | Morisaki et al. | |
| 5,948,944 A | 9/1999 | Zhang et al. | |
| 6,291,726 B1 | 9/2001 | Lee et al. | |
| 2007/0043244 A1 * | 2/2007 | Buettner | 568/708 |

FOREIGN PATENT DOCUMENTS

| | | | |
|---|---|---|---|
| CN | 1854114 | 11/2006 | |
| EP | 0 385 884 | 9/1990 | |
| EP | 0 779 270 | 6/1997 | |
| EP | 1 137 623 | 10/2001 | |
| EP | 1 509 496 | 3/2005 | |
| EP | 1 880 989 | 1/2008 | |
| EP | 1 935 870 | 6/2008 | |
| JP | 6157425 | * 6/1994 | ............ C07C 205/06 |
| WO | 92 11228 | 7/1992 | |
| WO | 92 15550 | 9/1992 | |
| WO | 99 42433 | 8/1999 | |
| WO | 02 30865 | 4/2002 | |
| WO | 03 045900 | 6/2003 | |
| WO | 2004 080587 | 9/2004 | |
| WO | 2005 037768 | 4/2005 | |
| WO | 2005 075407 | 8/2005 | |
| WO | 2008 086922 | 7/2008 | |
| WO | 2008 138784 | 11/2008 | |

OTHER PUBLICATIONS

Poirier, et al. Tetrahedron (1989), 45(5), 1415-22. (Derwent abstact provided).*
JP6157425, Derwent abstract, Jun. 1994, 2 pages.*
Babayon et al. Radiokimiya (1971), 13(4), 505-508; Derwent abstract provided.*
U.S. Appl. No. 13/109,399, filed May 17, 2011, Raichle, et al.
Olah, G. A., et al., "Nitration—Methods and Mechanisms," Chapter 1—Introduction and General Aspects, pp. 1-5, Chapter 2—Reagents and Methods of Aromatic Nitration / I.Acid-catalyzed electrophilic nitration, pp. 1-20, (1989).
Inoue, M., "Safe Nitrating Agent—Nitration of Benzene without Utilizing Strong Acids-," vol. 41, No. 12, pp. 832-835, (Mar. 1, 1993).
Franzyshen, S. K., et al., "Proton Acidity and Chemical Reactivity in Molten Salt Hydrates," The Journal of Physical Chemistry, vol. 94, No. 6, pp. 2684-2688, (1990).
International Search Report Issued Jul. 30, 2010 in PCT/EP10/052450 Filed Feb. 26, 2010.
U.S. Appl. No. 13/362,607, filed Jan. 31, 2012, Allardt, et al.

* cited by examiner

*Primary Examiner* — Clinton Brooks
(74) *Attorney, Agent, or Firm* — Oblon, McClelland, Maier & Neustadt, L.L.P.

(57) ABSTRACT

A process for the preparation of mononitroaromatics and dinitroaromatics, in which a hydrate melt of at least one metal nitrate $M(NO_3)_3$ is used as a nitrating medium, it being possible for M to be the metals Fe, Cr, Y, La, Ce, Al, Bi and In, and the metal nitrate having a water content of from 4 to 9 mol of water per $M(NO_3)_3$, leads to simplifications of the process and improved yields.

9 Claims, No Drawings

PROCESS FOR THE PREPARATION OF NITRATED AROMATICS AND MIXTURES THEREOF

The present invention relates to processes for the preparation of nitrated aromatics, in particular of mononitrobenzene (MB), mononitrotoluene (MNT), dinitrotoluene (DNT) and mixtures thereof.

The nitration of aromatics, such as benzene or toluene, with nitric acid-containing mixed acid has been known for decades. For the nitration of aromatics, as a rule the principle of synthesis by electrophilic aromatic substitution in the liquid phase is used (cf. G. A. Olah, K. Malhotra, et al. (1989), "Nitration—Methods and Mechanisms" VCH Weinheim, Cambridge).

The active agent used for the nitration is the nitryl cation $NO_2^+$, which is formed in a nitration system with the $NO_2^+$ carrier ($NO_2$—X, where X=Cl, OH, $OCH_3$, $O(CO)CH_3$, $NO_3$, etc.) by acid catalysis (protic Brönsted acids or aprotic Lewis acids) or can be used directly as nitronium salt (e.g. $(NO_2)BF_4$). The activity of a nitration system is decisively determined by the rate and concentration with which the $NO_2^+$ species can reach the substrate to be nitrated. The $NO_2^+$ species need not necessarily be present as a spectroscopically detectable free particle, as was shown in the nitration of toluene with $HNO_3/H_2SO_4$ mixtures. If the $NO_2^+$ carrier and the substrate are present in different liquid phases (heterogeneous reaction system), the nitration rate is also limited by the phase transfer of the $NO_2^+$ ion.

This relates in particular to the use of nitronium salts which are scarcely soluble in aromatics and other organic solvents. The extremely high nitration rates of the covalently bonded nitrates, such as $Ti(NO_3)_4$, $Sn(NO_3)_4$ and $VO(NO_3)_3$, are also due, inter alia, to the good miscibility with organic solvents or with the aromatics.

The required nitration activity for an aromatic depends substantially on the electronic activity of its substituents. In comparison with benzene, the term "aromatics activated for nitration" is used as the electron density is increased (alkylbenzenes, phenol) or the term "deactivated aromatics" is used if electron-attracting substituents are present, such as, for example, the nitro group itself.

In order in each case to introduce a nitro group into the compounds toluene, benzene, mononitrotoluene and mononitrobenzene, it is therefore necessary to work in this order with systems of increasing nitration activity. The same applies to other aromatics.

The substituents already present on the aromatic system also influence the position at which the nitro group is incorporated into the aromatic nucleus. In general, an isomer mixture typical of the respective substituent is obtained. Targeted variation of the isomer ratios by changing the nitration system has not been completely possible to date.

Since the preparation and handling of the very reactive nitronium salts and of the covalent, tetra- and pentavalent transition metal nitrates is technically complicated, nitric acid ($HNO_3$) is still the technically most important nitrating agent. The equilibrium (1) was decisive for the formation of the $NO_2^+$ ion:

$$2HNO_3 \leftrightarrow H_2NO_3^+ + NO_3^- \leftrightarrow NO_2^+ + NO_3^- + H_2O \qquad (1)$$

There is already a sufficiently high concentration of $NO_2^+$ ions present in a 100% strength nitric acid, and a high solubility of benzene, toluene and their nitro compounds results in high nitration rates even at temperatures below 0° C., as was shown for the formation of mononitrobenzene. Further proposed processes for the nitration of toluene to mono- and dinitrotoluene in homogeneous mixture with 100% strength $HNO_3$ (e.g. HoKo process) are based on this principle. However, the advantage of the high reaction rate in the homogeneous phase necessitates a complicated separation of the nitro compounds from the homogeneous phase after the reaction.

In the documents WO 1992/15550, WO 1992/11228, U.S. Pat. No. 5,099,078, U.S. Pat. No. 5,099,079 and U.S. Pat. No. 5,948,944, in each case reaction mixtures having large amounts of salt hydrates are used, resulting in the formation of a liquid salt hydrate phase and an organic phase as the second liquid phase.

WO 1992/15550 describes a continuous process for the synthesis of dinitrotoluene by reaction of the nitric acid with toluene. The reaction medium consists of nitric acid, water and the aromatic to be nitrated or the already nitrated aromatic. Here, the toluene is sprayed in portions into the continuous process.

The document WO 1992/11228 describes a continuous "one-pot" process for the preparation of dinitrotoluene by reaction of toluene and nitric acid. First, the toluene reacts with concentrated nitric acid and gives a product mixture comprising dinitrotoluene, unreacted nitric acid and water. The crude product mixture is then mixed with dehydrated, molten nitrate salt and further nitric acid is added to the mixture.

After phase separation in the vapor phase, the dinitrotoluene phase can be separated from the phase comprising the liquid, hydrated salts. The acidic vapor with the nitric acid and the liquid, hydrated salts are separated off and concentrated in order to recover the concentrated nitric acid. The nitrate salt solution is dehydrated and is recovered for reaction circulation. Metal nitrate hydrates and mixtures thereof are used, it being possible for the metals Ca, Li, Mg, Mn and Zn to be present.

U.S. Pat. No. 5,099,078 discloses a continuous "one-pot" process for the preparation of the product dinitrotoluene by reaction of toluene and nitric acid. In this process, the mononitration and the subsequent dinitration are carried out in processes connected in series. For the dinitration step, metal nitrate hydrates and metal nitrate mixtures in which the metals Na, K, Ca, Li, Mg, Mn and Zn may be present are used. The temperatures for the first nitration step are stated as being from 25 to 90° C.

U.S. Pat. No. 5,099,079 describes a method for separating off or for removing the acid impurities from a reaction solution which, in addition to the acid, also comprises the nitrated, aromatic products (such as mono- and dinitrotoluene). U.S. Pat. No. 5,099,079 describes in its examples mixtures of metal nitrate hydrates from Zn and Mg, from which the acid impurities are removed after the nitration reaction.

U.S. Pat. No. 5,948,944 describes the preparation of dinitrotoluene via a two-stage process which passes through a mononitration step. Owing to the phase separation between the mononitration and the dinitration, water of reaction can be recycled into the mononitration step. It is stated that the amount of water which is present during the mononitration step plays a key role for the amount of 2,4-dinitrotoluene which subsequently forms under dinitration, and that the amount of water also influences the mononitration rate.

U.S. Pat. No. 4,804,792 describes the nitration of benzene or toluene with nitrate salt melts. Nitrate salts of the metals Na, K, Li, which lead to mononitrobenzene or mononitrotoluene on reaction in the vapor phase reaction at temperatures of 150° C. to 250° C. and at a pressure of 100 mm Hg, are mentioned for this purpose.

Since water is formed during the nitration, the "concentration" of $NO_2^+$ ions decreases rapidly in the course of the reactions according to the equilibrium (1). In a pure HoKo process, it is therefore always only possible to work with a large excess of HNO₃ in relation to the aromatic.

However, this gives rise to the possibility of uncontrollable reactions and hence an increased cost and safety risk. Mixed acids (HNO₃ in concentrated sulfuric acid, nitrating acid) are therefore employed in industry, the water activity being kept at the necessary, low level via the $H_2SO_4$ concentration. For example, from 90 to 98% strength sulfuric acid is used for the dinitration of toluene. After nitration, the sulfuric acid must be concentrated again in a complicated distillation and temperatures up to 200° C. The simultaneous presence of residues of HNO₃, dissolved nitrous gases and organic ingredients complicates this process step. This also applies to the choice of material of the apparatuses and the working method.

In addition, a considerable amount of undesired byproducts, such as nitrocresols, is formed in the mixed acid process, which byproducts have to be washed out and removed.

For the HoKo process, EP-A 0 385 884 proposes the use of dehydrated and partially dehydrated sulfates of magnesium, of calcium, of zinc, of aluminum, of copper and of nickel for binding the water of reaction.

There has furthermore been no lack of attempts to find novel nitration systems which can be used on an industrial scale. Thus, the use of other acids was tested, for example of phosphoric acid instead of sulfuric acid. The use of zeolites has also been described. Differently treated or prepared silicates were also used for the nitration. Moreover, the use of borates in combination with $NO_2^+$ carrier systems was discussed.

U.S. Pat. No. 5,728,901 proposes the use of nitration catalysts in the form of water-tolerant Lewis acid catalysts of the general formula $Mn(L1)x(L2)y$, where M=lanthanoid element (La, Ce, Lu) or lithium and L1, L2=ligands in the form of perfluoroalkanesulfonates, fluorosulfonates, hexafluorophosphates and nitrates, it being possible to work with dilute HNO₃.

The use of room-temperature ionic liquids having organic cations (such as the classical imidazolium cation) as solvents for the nitrating medium is proposed in WO 2002/30865. These processes have the general disadvantage that the liquids themselves are also partly nitrated.

The authors M. Inoue et al. (M. Inoue (1993), "Safe nitrating agent; Nitration of benzene without utilizing strong acids", Kagaku to Kyoiku 41(12), 832-835) describe a nitrating reagent for benzene without use of strong acids. Nitrate sources used there are metal nitrate hydrates, the metals being Mg, Ni, Zn, Al, Cr and Fe. In addition, $B_2O_3$ immobilized on silica gel is used.

In U.S. Pat. No. 6,291,726 and WO 1999/42433, oxides, silicates, zeolites and basic salts, for example of iron, having a large specific surface area, are used for the nitration of toluene directly with nitrogen oxide with simultaneous action of oxygen under pressures of 3-8 bar to give dinitrotoluene. A substantial economic point of view of the nitration of toluene is the isomer distribution, both in the case of mononitrotoluene and in the case of dinitrotoluene. The largest part of the MNT and DNT produced is reduced to the corresponding mixture of isomeric amines and then converted into the isocyanates. These are starting materials for polyurethane production.

In these processes, the end users expect an isomer mixture of TDI with 80 mol % of 2,4-TDI and 20 mol % of 2,6-TDI, as obtained in the classical mixed acid processes operated at present. From other points of view, however, a targeted variation and improvement of the isomer ratio would be desirable. However, it has not been possible to date to realize this with the known nitrating systems.

Inorganic salt hydrate melts, such as $\{Ca(NO_3)_2{}^x 4H_2O\}$, to which a little HNO₃ has been added are characterized as an independent nitrating medium in the technical literature, so that they can be used as selective nitrating agents for the mononitration, since the reactivity for a further nitration stage is not sufficient in the case of aromatics (cf. S. K. Franzyshen, M. D. Schiavelli, et al. "Proton Acidity and Chemical Reactivity in Molten Salt Hydrates", Journal of Physical Chemistry (1990), 94(6): 2684-2688). There, the proton activity and chemical reactivity of nitrate ions in molten salt hydrates are described. Here, melts of $M(NO_3)_3 {}^* XH_2O$ are used for the nitration of toluene, it being possible for M to be Ca, Cd, Al and zinc. The reaction temperature is, for example, 75° C.

CN-A 1854 114 presents the use of bismuth nitrate pentahydrate and iron(III)nitrate nonahydrate as nitrating reagents, in particular for activated aromatics, such as phenols and amines. However, the nitration of toluene is also mentioned. The nitration is said to be effected on the one hand with solid hydrates at low temperatures and on the other hand in a liquid system. In the case of the nitration of toluene in a liquid system, only an 83% conversion to mononitrotoluene is achieved at a temperature of 125° C. after a reaction time of 5 hours (on an mg scale); however, none of the examples describes a dinitration.

An object of the present invention is to provide a process and a nitrating medium which permit the mononitration of aromatics, in particular benzene and toluene, and the further nitration of nitroaromatics, such as of nitrotoluenes to dinitrotoluenes, facilitate the removal of the water of reaction and can furthermore also be used on an industrial scale. The environmental compatibility, safety and cost situation are also to be improved.

It has now surprisingly been found that these objects can be achieved by the use of the melts of the following hydrates:

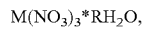

in which
M is Fe, Cr, Y, La, Ce, Al, Bi, In, and
4≤R≤9.

The water-content normally is 4 to 9 mol, often 4 to 7 mol, per mole of metal nitrate.

Moreover, mixtures of the metal nitrate hydrates can be used as a reaction medium if their reactivity is appropriately adjusted. With a suitable chosen melt composition, up to 100% conversion of the aromatic is achieved both for the mononitration and for the dinitration. The hydrate melts of iron(III) and chromium(III) nitrate have proven particularly suitable for the nitration reactions.

The reactivity is controlled in particular via the water content of the hydrate melt, the choice of the cation composition, the temperature and the addition of HNO₃. The nitration activity increases as a rule with decreasing water content of the melt, the meltability of the hydrates and the hydrolysis reactions of the metal nitrates setting lower limits for the water contents.

These are frequently from 4 to 7 mol of $H_2O$ per mole of metal nitrate but are in particular salt-specific and can be further reduced by mixing of said salt hydrates, admixing of nitrates of mono- and divalent metals and their hydrates and the addition of nitric acid for the respective main component of the trivalent nitrate. Although the melting point can be reduced or the water content can be reduced by the admixing of the nitrates of mono- or divalent metals, such as Li, Na, K, Mg, Ca, Cu or Zn, these salts simultaneously act to reduce the reactivity for a given temperature and water content.

The invention relates in particular to a process for the preparation of mononitroaromatics, dinitroaromatics and/or mixtures thereof, in which a hydrate melt of at least one metal nitrate $M(NO_3)_3$ is used as a nitrating medium in the preparation, M being the metals Fe, Cr, Y, La, Ce, Al, Bi and In, and the metal nitrate preferably having a water content of from 4 to 9 mol, often from 4 to 7 mol, of water per $M(NO_3)_3$.

In particular, those organic compounds which comprise a nitro group ($—NO_2$) on an aromatic ring are designated as mononitroaromatics. Those compounds which comprise two nitro groups ($—NO_2$) on an aromatic ring are designated as dinitroaromatics. Aromatics are to be understood as meaning the compounds known to the person skilled in the art (in particular Hückel aromatics), for example monocyclic aromatics, such as the compounds such as benzene, phenol, aniline, toluene, xylene; or bicyclic aromatics, such as naphthalene or substituted variants thereof. Unsubstituted or monosubstituted aromatics are particularly preferred as aromatic starting materials, and benzene or toluene is especially preferred.

The process according to the invention relates in particular to a process by means of which mononitrobenzene (MB), mononitrotoluene (MNT), dinitrotoluene (DNT) and mixtures thereof are prepared, the nitrating medium used being a hydrate melt of at least one metal nitrate $M(NO_3)_3$, M being the metals Fe, Cr, Y, La, Ce, Al, Bi and In, and the metal nitrate having in particular a water content of from 4 to 9 mol, often from 4 to 7 mol, of water per $M(NO_3)_3$.

In a preferred embodiment of the present invention, the process is carried out in a temperature range from 30° to 200° C., in particular from 70° to 125° C., often from 80° to 110° C.

In the process according to the invention, nitrates of the metals Fe, Cr, Bi and In or mixtures of these nitrates can preferably be used as metal nitrates $M(NO_3)_3$. In the process according to the invention, in particular nitric acid and/or nitrates of metals of higher and/or lower valency (e.g. of the valency 1, 2 or 4) can be added as an additional component to the hydrate melt.

The process according to the invention comprises in particular a process step in which additional nitric acid is added to the hydrate melt, this being added to the hydrate melt preferably in the form of a 20 to 100% strength aqueous solution of $HNO_3$, effected by reaction of the hydrate melt with gaseous or liquid nitrogen dioxide or by addition of other acids.

In one embodiment, the process according to the invention is distinguished in that the nitration is effected by removing the water of reaction during and/or after the reaction, and in that the nitrate consumed is replenished by addition of nitric acid and/or NOx (with or without addition of $O_2$).

The invention also relates to an embodiment of the process in which the contents of undesired byproducts, in particular trinitrotoluene (TNT) and nitrocresols, in the reaction product are in each case less than 100 ppm.

The invention also relates to the products obtained by the process, in particular the mononitroaromatics and dinitroaromatics characterized by a high purity, and mixtures thereof.

The invention also relates to the further use of the prepared nitroaromatics as precursors for the preparation of the aromatic amines, diamines, mono-isocyanates and/or diisocyanates. For the preparation of these diamines, the dinitroaromatics produced are reduced by classical processes. These aromatic diamines can then be converted into the corresponding diisocyanates by classical processes.

It was also surprisingly found that the reactivity can be increased by small additions of nitrates or oxynitrates with metals in the valency states +4 (in particular Zr, Hf, Ce) or +5 (in particular Bi, Sb) and hydrates thereof. These metal nitrates can be used as single component or as a combination of the metal nitrates of Fe, Cr, Bi, etc mentioned above.

In addition, it was found that, for carrying out the nitration reactions, the hydrate melt need not be completely clear but may comprise suspended metal nitrate, undissolved hydrate having relatively low water content or partially hydrolyzed metal nitrate. The reaction temperatures can preferably be chosen from 30° C. to 200° C., in particular from 70° C. to 125° C., often from 80° to 110° C., depending on the requirements for the nitration reaction.

The working examples mentioned below illustrate the reaction conditions for nitration and the product spectrum achieved by the processes.

The isomer distribution often is in the range from 50 to 70 mol % of o-NT and from 30 to 45 mol % of p-NT in the case of MNT and the range from 60 to 90 mol % of 2,4-DNT in the case of DNT. An advantage of using the salt hydrate melts as nitrating medium is that normally less than 100 ppm of nitrocresols are formed. TNT contents caused by trinitration remain normally below 100 ppm. The avoidance of TNT and in particular of 2,4,6-TNT is of advantage.

The aromatics and nitroaromatics have only a low solubility in the salt hydrate melts up to the stated maximum temperature, so the reactions can typically be carried out in a 2-phase mixture of aromatics and melt with thorough mixing, it being possible for the reaction to be carried out in the batch mode or continuously. The use of inert solvents (such as alkanes or haloalkanes) is possible.

The reduction of the reactivity during the reaction by the consumption of $HNO_3$ or nitrate and the formation of water and/or hydroxide can be counteracted by, depending on the reaction procedure, choosing the molar nitrate/aromatic ratio appropriately, metering in $HNO_3$ and/or metal nitrate subsequently and/or separating off the water of reaction, for example by distillation, membrane evaporation or other methods in the form of dilute nitric acid, either directly from the reactor or in a downstream regeneration step of the salt hydrate melt.

Typical molar nitrate/aromatic ratios are as a rule from 0.5 to 20, preferably from 5 to 10.

The regeneration of the salt hydrate melt often consists substantially in distilling off the nitric acid from the melt and/or adding a more highly concentrated nitric acid to the melt, or the solidified salt hydrate is used for neutralizing resulting hydroxide in order to reestablish the initial water and $HNO_3$ content. The nitric acid required for regenerating the melt may be produced in situ in the salt hydrate melt partly or completely also by passing in nitrous gas mixtures with air or oxygen.

Furthermore, the invention also comprises the further process steps of working-up of the nitroaromatics according to the processes known to a person skilled in the art. These are in particular the phase separation and the working-up of the organic phase, preferably one or more washes with subsequent phase separations. In principle, such processes are described, for example, in Ullmann, 6$^{th}$ edition, Encyclopedia of Industrial Chemistry, Vol. 23, Wiley 2003. Descriptions are also to be found in EP-A 1 880 989 or WO 2005/075407.

In general, the hydrogenation of the nitro compounds to the corresponding amines follows. Such reductions are described by way of example in EP-A 1 137 623, WO 2008/138784, WO 2005/037768 or EP-A 1 935 870.

This is generally followed by the conversion of the amines obtained into the corresponding isocyanates, for example by a gas-phase or liquid-phase phosgenation process. Such reactions are described by way of example in WO 2003/045900, WO 2008/086922, EP-A 1 509 496 and WO 2004/080587.

The process according to the invention permits in particular processing of the aromatic starting materials and products in a relatively large volume (e.g. pilot or production scale) according to the safety guidelines.

EXAMPLE 1

Mononitration of Benzene with a Hydrate Melt of Iron(III) Nitrate

In a 500 ml two-necked flask having a reflux condenser, 0.15 mol (13.3 ml) of benzene and 1.5 mol (525 g) of iron(III) nitrate hydrate having a water content of 6 mol of water per mole of salt were reacted for 5 h with stirring by means of a KPG stirrer at a reaction temperature of 80° C. The organic phase was diluted with xylene in the ratio 1:10 after the phase separation and was analyzed by means of gas chromatography and comprised 98.23 mol % of mononitrobenzene and also 1.77 mol % of benzene. 1,3-Dinitrobenzene was found only in traces.

EXAMPLE 2

Mononitration of Toluene with a Hydrate Melt of Iron(III) Nitrate 20 mmol (2.1 ml) of toluene, 30 mmol (1.3 ml) of 96.77% strength $HNO_3$ and 200 mol (66.39 g) of $Fe(NO_3)_3 5H_2O$ were reacted for 15 min with stirring by means of a KPG stirrer (1400 $min^{-1}$) at a reaction temperature of 100° C. The organic phase was diluted with xylene in the ratio 1:10 after the phase separation and was analyzed by means of gas chromatography. In addition to 0.97 mol % of toluene, it comprised 98.19 mol % of mononitrotoluene having the isomer composition o:m:p=55.42:5.52:38.5. 0.53 mol % of phenylnitromethane (α-nitrotoluene) and 0.29 mol % of benzaldehyde were found as byproduct.

EXAMPLE 3

Mononitration of Toluene with a Hydrate Melt of Chromium(III) Nitrate 0.1 mol (10.6 ml) of toluene and 0.1 mol (34.34 g) of chromium(III) nitrate hydrate, having a water content of 6 mol of water per mole of salt, were reacted in a 250 ml three-necked flask for 5 h with stirring by means of a KPG stirrer at a reaction temperature of 100° C. The organic phase was analyzed by means of Raman spectroscopy after the phase separation and, after the reaction, comprised 35.3 mol % of 2-nitrotoluene and 15.0 mol % of 4-nitrotoluene. 4.5 mol % of phenylnitromethane (α-nitrotoluene) were found as a byproduct by NMR spectroscopy.

EXAMPLE 4

Nitration of 2-Nitrotoluene With a Hydrate Melt of Iron(III) Nitrate 0.25 mol (30 ml) of 2-nitrotoluene, 0.25 mol (10.7 ml) of 96.77% strength nitric acid and 2.5 mol (827.5 g) of iron(III) nitrate hydrate, having a water content of 5 mol of water per mole of salt, were reacted in 1 l double-jacket vessel for 9 h with stirring by means of a KPG stirrer (1000 $min^{-1}$) at a reaction temperature of 100° C. The organic phase was analyzed by means of gas chromatography after the phase separation and comprised 8.5 mol % of 2-nitrotoluene, 91.19 mol % of dinitrotoluenes (2,4-DNT:2,5-DNT:2,6-DNT=66.50:0.37:33.13) and, as byproducts, 0.01 mol % of 2-nitrobenzaldehyde and 0.14 mol % of dinitrobenzaldehydes.

EXAMPLE 5

Nitration of 2-Nitrotoluene With a Hydrate Melt of Iron(III) Nitrate 5 mmol (0.59 ml) of 2-nitrotoluene, 7.5 mmol (0.32 ml) of 96.77% strength nitric acid and 50 mmol (16.235 g) of $Fe(NO_3)_3 5H_2O$ were reacted in a 25 ml flask for 2 h with stirring by means of a dispersing tool (IKA-ULTRA-TURRAX®T 25 basic, 19 000 $min^{-1}$) at a reaction temperature of 100° C. The organic phase was diluted with xylene in the ratio 1:10 after the phase separation and analyzed by means of gas chromatography and comprised 58.48 mol % of 2-nitrotoluene, 40.57 mol % of dinitrotoluenes (2,4-DNT:2,5-DNT:2,6-DNT=66.97:0.30:32.73) and, as byproducts, 0.41 mol % of 2-nitrobenzaldehyde and 0.14 mol % of dinitrobenzaldehydes.

EXAMPLE 6

Nitration of 2-Nitrotoluene With a Hydrate Melt of Bismuth(III) Nitrate 25 mmol (2.9 ml) of 2-nitrotoluene, 250 mmol (121.27 g) of $Bi(NO_3)_3 5H_2O$ were reacted in a 250 ml round-bottomed flask for 9 h with stirring by means of a magnetic stirrer at a reaction temperature of 100° C. The organic phase was diluted with xylene in the ratio 1:10 after the phase separation and analyzed by means of gas chromatography and comprised 50.7 mol % of 2-nitrotoluene and 48.3 mol % of dinitrotoluenes (2,4-DNT:2,6-DNT=63.56:36.44).

EXAMPLE 7

Nitration of 2-Nitrotoluene With a Hydrate Melt of Indium(III) Nitrate 5 mmol (0.59 ml) of 2-nitrotoluene, 7.5 mmol (0.32 ml) of 96.77% strength $HNO_3$ and 50 mmol (19.095 g) of $In(NO_3)_3$ 4.5$H_2O$ were reacted in a 50 ml round-bottomed flask for 9 h with stirring by means of a magnetic stirrer at a reaction temperature of 100° C. The organic phase was diluted with xylene in the ratio of 1:10 after the phase separation and analyzed by means of gas chromatography and comprised 60.47 mol % of 2-nitrotoluene and 38.31 mol % of dinitrotoluenes (2,4-DNT:2,5-DNT:2,6-DNT=70.00:0.26:29.73). 0.74 mol % of 2-nitrobenzaldehyde and 0.07 mol % of dinitrobenzaldehydes were found as byproducts.

EXAMPLE 8

Nitration of Toluene to DNT With a Hydrate Melt of Iron(III) Nitrate 20 mmol (2.12 ml) of toluene, 30 mmol (1.3 ml) of 96.77% strength nitric acid and 200 mmol (66.39 g) $Fe(NO_3) 5H_2O$ were reacted in a 250 ml flask for 99 h with stirring by means of a KPG stirrer (1400 $min^{-1}$) at a reaction temperature of 100° C. The organic phase was diluted with xylene in the ratio 1:10 after the phase separation and analyzed by means of gas chromatography and comprised 1.67 mol % of mononitrotoluene (0.33% of oNT, 0.18% of mNT, 1.16% of pNT), 98.18 mol % of dinitrotoluenes (74.74% of 2,4-DNT, 0.71% of 2,5-DNT, 19.47% of 2,6-DNT, 3.02% of 3,4-DNT and 0.25% of 3,5-DNT) with an isomer ratio of 2,4-DNT:2,6-DNT=79.33:20.67, and, as byproducts, 0.02 mol % of 2-nitrobenzaldehyde, 0.04 mol % of 4-nitrobenzaldehyde and 0.14 mol % of dinitrobenzaldehydes.

EXAMPLE 9

Nitration of Dinitrotoluene to TNT With a Hydrate Melt of Iron(III) Nitrate 0.25 mol (45.535 g) of 2,4-dinitrotoluene, 0.25 mol (17.9 ml) of 65% strength nitric acid and 2.5 mol (785 g) of iron(III) nitrate hydrate, having a water content of 4 mol of water per mole of salt, were reacted in a 1 l double-jacket vessel for 9 h with stirring by means of a KPG stirrer (1000 min$^{-1}$) at a reaction temperature of 100° C. The organic phase was diluted with xylene in the ratio of 1:10 after the phase separation and analyzed by means of gas chromatography. No 2,4,6-trinitrotoluene could be detected.

We claim:

1. A process, comprising:
   reacting a hydrate melt with mononitrotoluene, to form dinitrotoluene,
   wherein:
   the hydrate melt comprises $Fe(NO_3)_3$, which acts as a nitrating medium, and has a water content of from 4 to 5 mol of water per $Fe(NO_3)_3$.

2. The process of claim 1, wherein the process occurs in a temperature range from 30° C. to 200° C.

3. The process of claim 1, wherein the hydrate melt further comprises at least one additional component selected from the group consisting of nitric acid, a nitrate with a metal of higher valency, and a nitrate with a metal of lower valency.

4. The process of claim 1, wherein the hydrate melt further comprises additional nitric acid added to the hydrate melt in the form of a 20 to 100% strength aqueous solution of $HNO_3$, which is produced by reaction of the hydrate melt with gaseous or liquid nitrogen dioxide or by addition of at least one other acid.

5. The process of claim 1, wherein nitration is affected by removing water of reaction during or after the reaction, and wherein a nitrate consumed is replenished by addition of at least one oxidant selected from the group consisting of nitric acid, NO, and $NO_2$ with or without addition of $O_2$.

6. The process of claim 1, wherein a content of trinitrotoluene (TNT) and a content of at least one nitrocresol in the reaction product are, in each case, less than 100 ppm.

7. The process of claim 1, wherein nitration is affected by removing water of reaction during and after the reaction, and wherein a nitrate consumed is replenished by addition of at least one oxidant selected from the group consisting of nitric acid and NO, and $NO_2$ with or without addition of $O_2$.

8. The process of claim 1, wherein the $Fe(NO_3)_3$ has a water content of 4 mol of water per $Fe(NO_3)_3$.

9. The process of claim 1, wherein the $Fe(NO_3)_3$ has a water content of 5 mol of water per $Fe(NO_3)_3$.

* * * * *